United States Patent [19]

Hackett

[11] Patent Number: 5,392,909
[45] Date of Patent: Feb. 28, 1995

[54] RELEASABLE UNIVERSAL BLISTER PACKAGE FOR ELONGATED SURGICAL DEVICES

[75] Inventor: Robert C. Hackett, Tampa, Fla.

[73] Assignee: Linvatec Corporation, Largo, Fla.

[21] Appl. No.: 147,184

[22] Filed: Nov. 3, 1993

[51] Int. Cl.⁶ .............................................. B65D 83/00
[52] U.S. Cl. ................................... 206/363; 206/438
[58] Field of Search ............. 206/363, 364, 467, 469, 206/471, 486, 564, 438

[56] References Cited

U.S. PATENT DOCUMENTS

| | | |
|---|---|---|
| 3,301,392 | 1/1967 | Regan, Jr. . |
| 3,696,920 | 10/1972 | Lahay . |
| 3,983,996 | 10/1976 | Hendren, III ................. 206/564 |
| 4,101,031 | 7/1978 | Cromie . |
| 4,111,302 | 9/1978 | Roth ............................. 206/363 |
| 4,216,860 | 8/1980 | Heimann . |
| 4,324,331 | 4/1982 | Ignasiak . |
| 4,524,868 | 6/1985 | Buckley et al. .............. 206/364 |
| 4,657,138 | 4/1987 | Watson . |
| 4,730,729 | 3/1988 | Monch . |
| 4,746,614 | 5/1988 | Devaney, Jr. et al. ....... 206/564 X |
| 4,807,752 | 2/1989 | Chodorow . |
| 5,031,775 | 7/1991 | Kane ............................. 206/438 X |
| 5,082,112 | 1/1992 | Dunklee ....................... 206/363 |
| 5,131,537 | 7/1992 | Gonzales ..................... 206/564 X |
| 5,133,454 | 7/1992 | Hammer ....................... 206/364 |
| 5,176,258 | 1/1993 | Antal . |
| 5,246,109 | 9/1993 | Markle et al. ................ 206/363 |

OTHER PUBLICATIONS

Techform Does It All!, Packaging Reference Issue, 1986, vol. 31, p. 134.

Primary Examiner—Paul T. Sewell
Assistant Examiner—Ted Kavanaugh
Attorney, Agent, or Firm—Gene Warzecha

[57] ABSTRACT

A single size, universal-type container capable of receiving any one of a variety of elongated medical devices such as rotatable arthroscopic shaver blades, drills, pins, wires and the like. The container has a generally trapezoidal transverse cross-section tapering inwardly from an open end at which a cover or lid may be heat-sealed. The trapezoidal shape enables the container to receive elongated cylindrical devices having different diameters. The container is provided with a pair of longitudinally spaced locking stations, each provided with a plurality of opposed arcuate wall sections for engaging opposite sides of the elongated medical device. The arcuate wall sections of each locking station vary in size from the bottom opening of the container such that the smallest diameter elongated medical devices are retained deep within the container while the largest diameter medical devices are retained closer to the opening of the container. A pair of laterally spaced trigger tabs are molded on the outside of the top wall of the container. The peripheral container wall interconnects the arcuate wall sections to the trigger tab associated with that section such that squeezing the tabs opens the gap between the arcuate wall sections to release the device.

16 Claims, 9 Drawing Sheets

RELEASABLE UNIVERSAL BLISTER PACKAGE FOR ELONGATED SURGICAL DEVICES

BACKGROUND OF THE INVENTION

1. Field of the Invention

The invention relates to sealed packages for securely holding medical devices to prevent their movement within the package. More particularly, the invention relates to a sterilizable blister package for securely holding one of a variety of sizes of elongated medical devices and releasing the device after the package is opened. Still more particularly, the invention relates to a package for holding one of a variety of tubular elongated medical devices having various diameters.

2. Description of the Prior Art

Sealed blister containers for holding products are commonly used for a variety of products including medical and surgical devices and instruments. Such containers are generally made by thermoforming, vacuum-forming, injection molding or similarly shaping a polymeric material into a housing having a cavity with the desired shape to contain a particular article. The containers are particularly useful for holding medical devices because they enable sterilization of the contents and can be made transparent and in a variety of unique shapes.

The housing is generally formed with at least one open end which is adapted to be sealed with a cover or lid which can be opened without touching (and thereby contaminating) the contents. The lid is normally heat-sealed to a peripheral flange around the open end of the housing and is generally made from a flexible material such as TYVEK ® (a registered trademark of Dupont) which is a spun-bonded polyolefin.

Several design considerations are addressed in developing containers for packaging medical devices in such pre-formed blisters. First of all, it is often necessary to secure the device from movement within the package. Such movement may either damage the device, break the seal and compromise the sterility of the device or create undesirable particulate matter within the package which could contaminate the sterile surgical field when the package is opened. In order to securely hold the device in a given package, the housing cavity is often provided with suitably shaped supporting surfaces to minimize the movement of the device in the cavity. The function of these surfaces may be supplemented by including within the package a protective device such as a separate compressible insert, for example, polyurethane foam. Another concern with blister packages for medical devices is that any protective devices within the cavity should remain within the cavity when the lid is opened so the protective devices do not fall into the sterile field during a surgical procedure. In addition to the foregoing concerns about product movement and loose protective devices, it is desirable to produce a universal-type package which is able to accommodate differently sized products. This enhances efficiency by minimizing production costs.

An additional disadvantage of prior art containers is their inability to retain and easily release a product after the lid has been removed. It would be advantageous to have a package which could be opened and could still retain a device until the user triggers its release without having to touch the device.

Some prior art devices are known which address some of these design considerations, but not all. Ignasiak U.S. Pat. No. 4,324,331, for example, discloses an elongated blister package for containing an elongated surgical implement such as a drill bit, pin or wire. The package is produced with an elongated cavity having a plurality of longitudinally spaced areas in the cavity for enabling one packaging cavity to be used for various lengths of the implements. Each of the spaced areas is adapted to receive a separate protective plastic or rubber plug insert at each end of the implement to prevent it from moving and penetrating the ends of the cavity.

While the Ignasiak patent shows a universal-type of package for receiving a variety of different-length elongated devices, there is no known device which would enable the production of a single package which could receive a variety of different-diameter elongated devices. Moreover, Ignasiak utilizes undesirable separable inserts.

Antal U.S. Pat. No. 5,176,258, assigned to the assignee hereof, discloses a sealed package containing a flexible insert secured to the package lid. The Antal package is also sized to receive a variety of sizes of products, but includes separable foam inserts which add to package expense and which produce some risk of coming loose.

Heimann U.S. Pat. No. 4,216,860 discloses another medical device container in which the protective insert is secured to the lid. This package has a flexible insert affixed to a backing sheet which is bonded to a peripheral flange and is also adapted to be opened manually—upside down—to dispense the contents onto a sterile field without the need of manual contact. Removal of the backing sheet pulls the flexible insert out of the package thereby enabling the medical device to fall freely onto a sterile location. The Heimann package requires separable inserts, is not adapted to a variety of product sizes and does not have a product releasing trigger mechanism.

It is accordingly an object of this invention to produce a storage container for securely holding relatively rigid elongated medical devices without the need for any component packaging parts other than the container and its lid.

It is an object of this invention to produce a blister package for receiving a product, in particular a surgical product, wherein the package has an integrally formed structure enabling the retention of the product within the package without any other non-integrally formed devices such as polyurethane foam inserts, etc.

It is a further object of this invention to produce a two-part blister package for receiving a surgical product, the package parts being a cavity-defining blister having a peripheral flange (i.e. first part) and a cover or lid secured to the flange (i.e. second part) wherein the cavity is capable of receiving and securing a plurality of different diameters of tubular surgical products.

It is still another object of this invention to produce a blister package having an integrally formed, releasable friction fitting means for securely holding an elongated surgical product and a trigger structure for releasing such product without manually contacting the product.

It is also an object of this invention to produce a two-part storage container for elongated medical devices having a cutting means at one end of the device, the container capable of isolating the sharp elements of the cutting means from adjacent container walls without requiring any auxiliary inserts or other components.

It is another object of this invention to produce a package incorporating all of the aforementioned features and made from a material which enables sterilization of the package contents.

SUMMARY OF THE INVENTION

These and other objects of this invention are achieved by the preferred embodiment disclosed herein which is a storage container for containing an elongated product comprising a housing having an elongated cavity for receiving an elongated device along an axial plane thereof. The cavity is defined by a peripheral wall having a closed top end, a bottom rim surrounding an open bottom end and a side wall extending between the top end and the bottom rim. The container has locking means for releasably, frictionally and directly engaging an elongated device within the housing and the locking means is integrally formed with the peripheral wall of the housing. A trigger means is provided for being selectively actuated to release the locking means to thereby disengage an elongated device engaged by the locking means. The trigger means comprises a pair of laterally spaced finger tabs integrally molded with the closed top end of the peripheral wall, one on each side of the axial plane, and interconnecting means for joining the pair of finger tabs and the locking means to enable motion of the pair of tabs to disengage the locking means.

In the preferred embodiment disclosed herein, the locking means comprises at least one pair of opposed wall sections of predetermined longitudinal length extending laterally inwardly from opposite sides of said peripheral wall and normally spaced a predetermined lateral distance for thereby frictionally engaging a portion of an elongated device between said opposed wall sections.

DESCRIPTION OF THE PREFERRED EMBODIMENT

Figure 1:
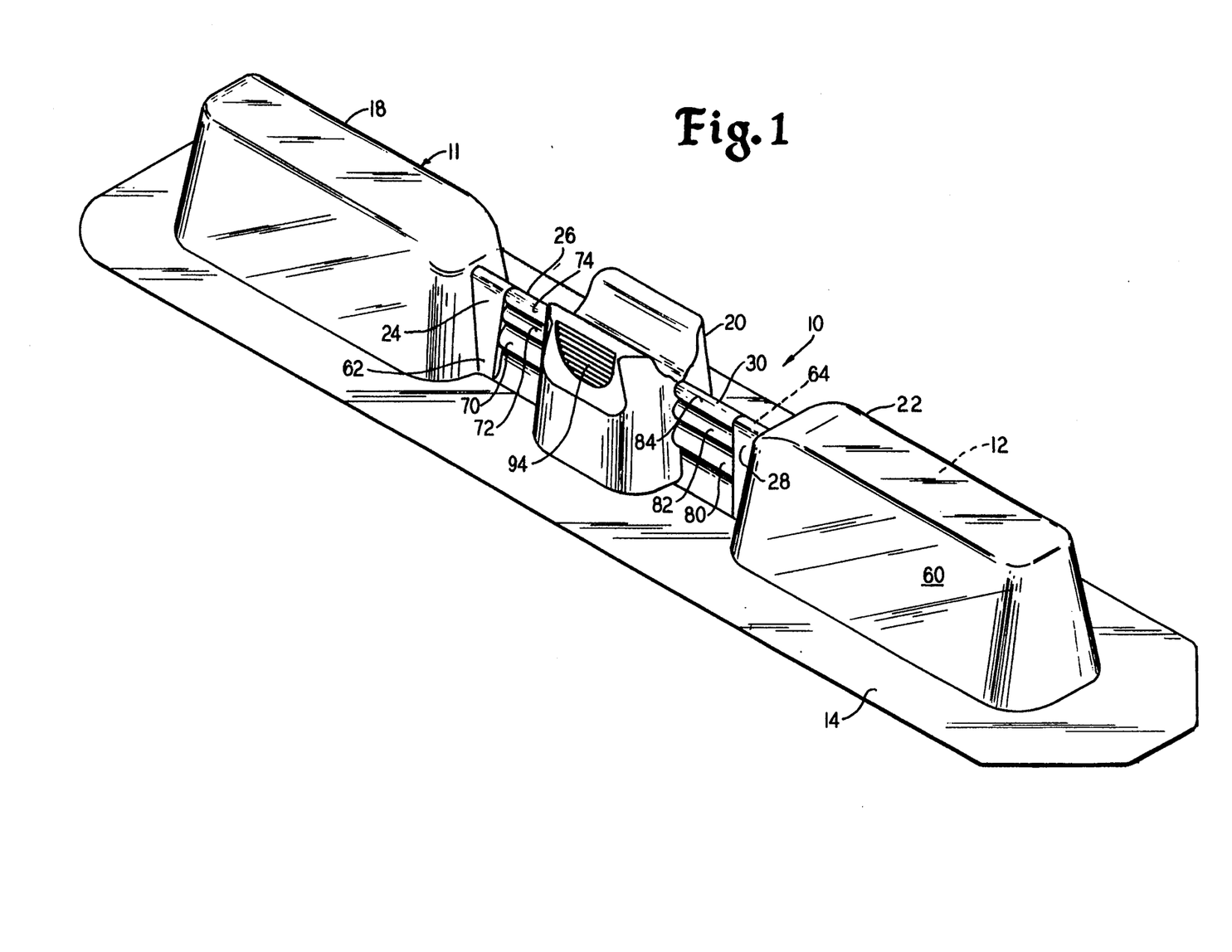
FIG. 1 is a top perspective view of a package constructed in accordance with the principles of this invention.
Figure 2:
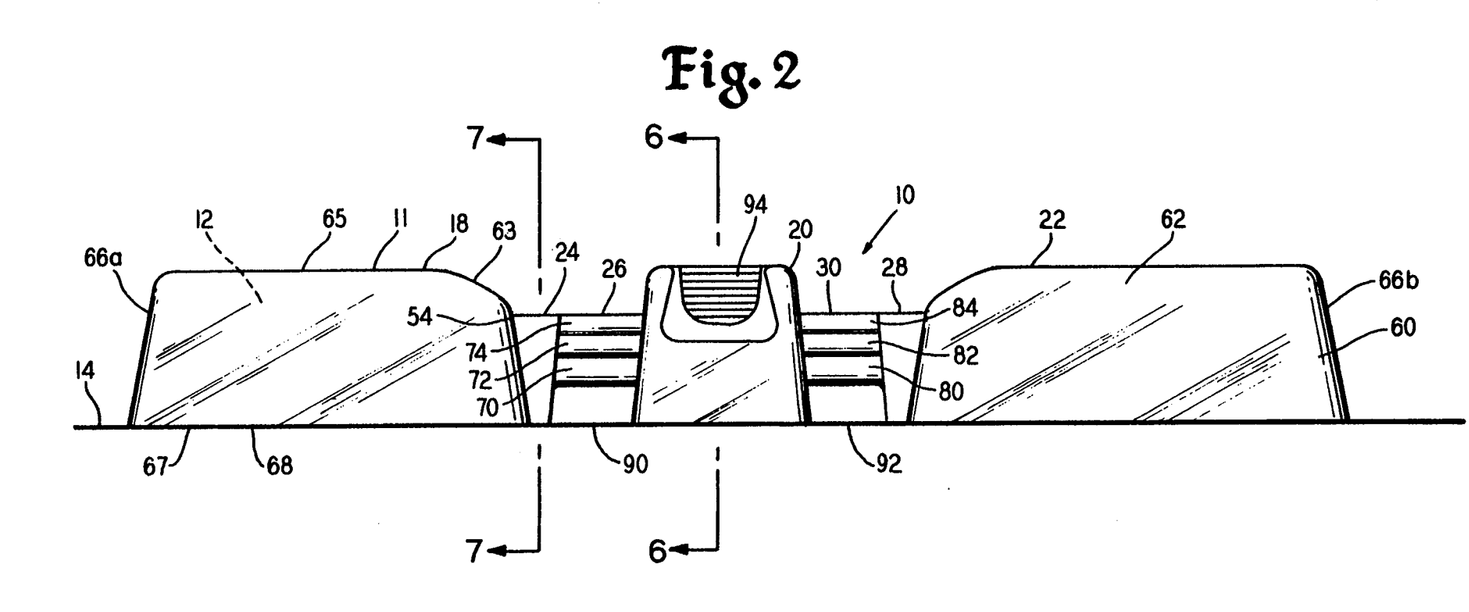
FIG. 2 is a side elevation view of the package of FIG. 1.
Figure 3:
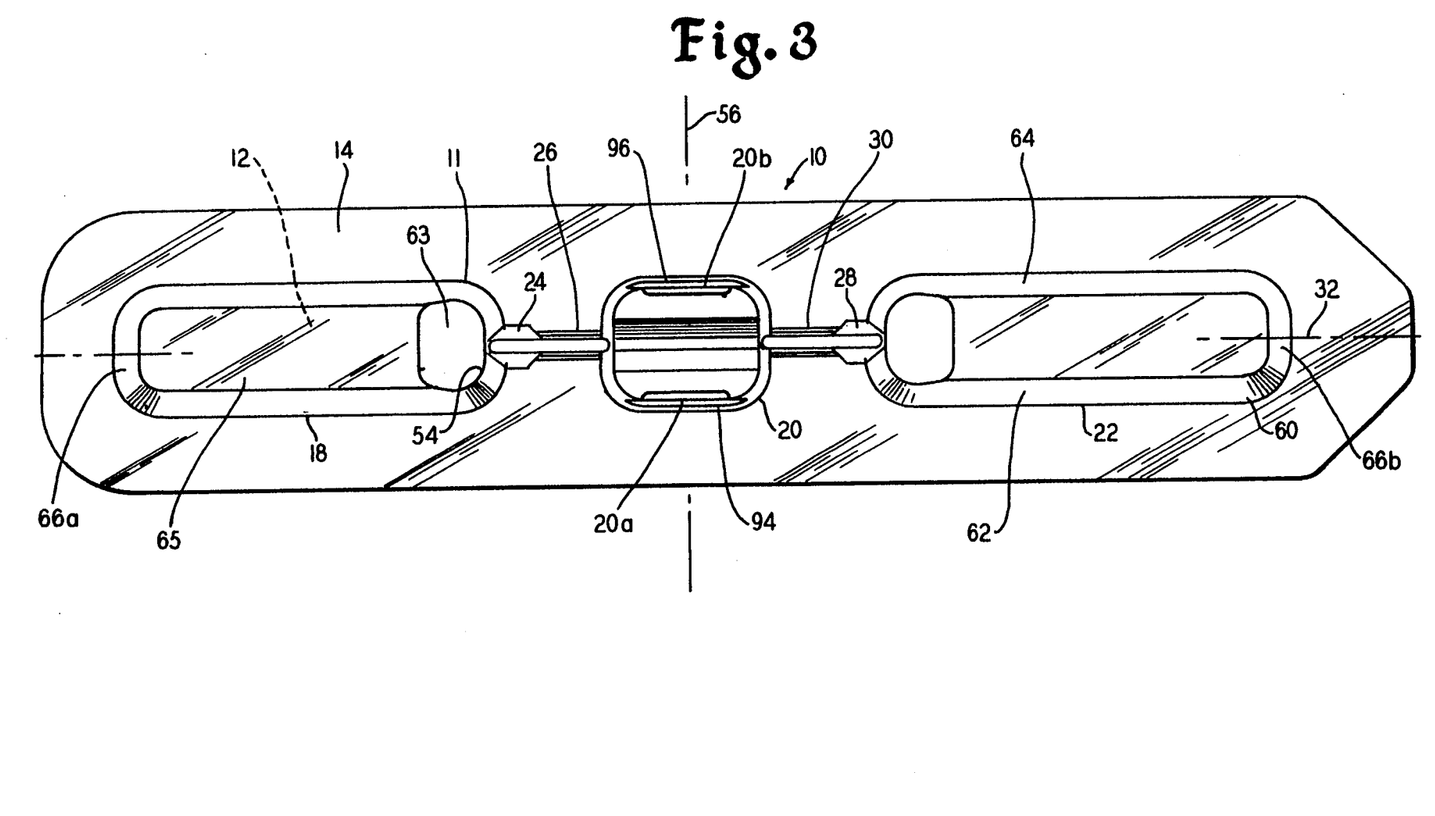
FIG. 3 is a plan view of FIG. 1.
Figure 4:
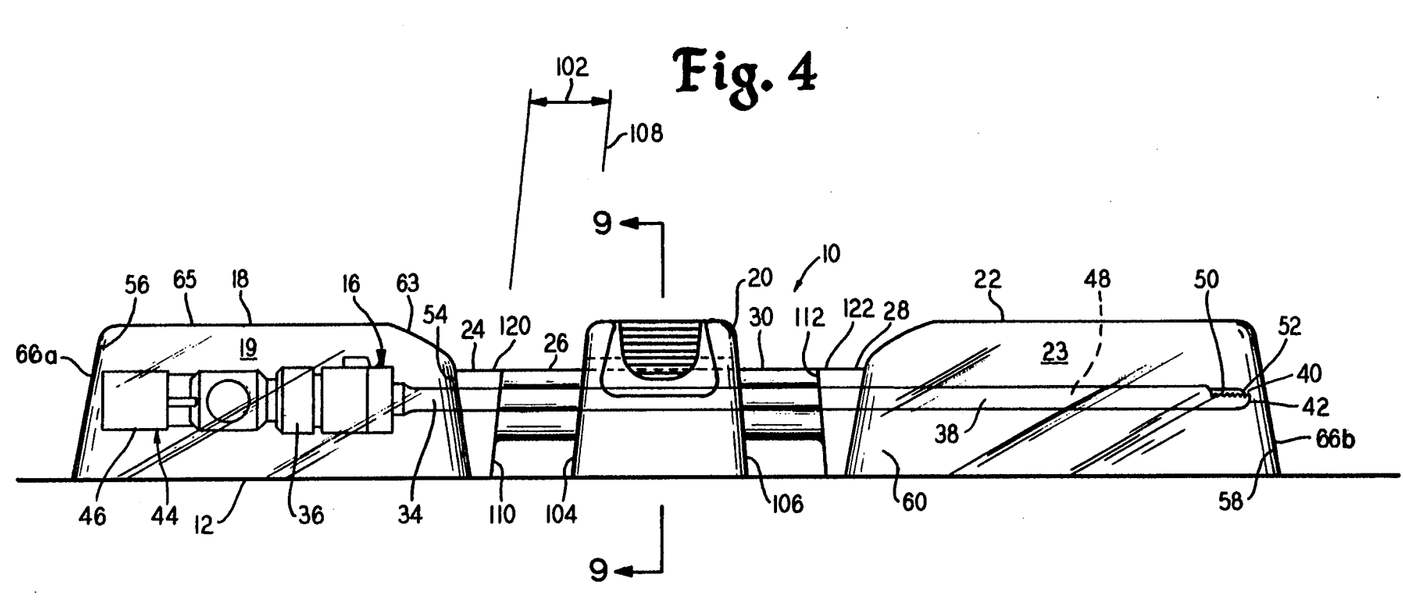
FIG. 4 is a side elevation view of a transparent package of FIG. 1 with an elongated arthroscopic shaver blade shown therein.
Figure 5:
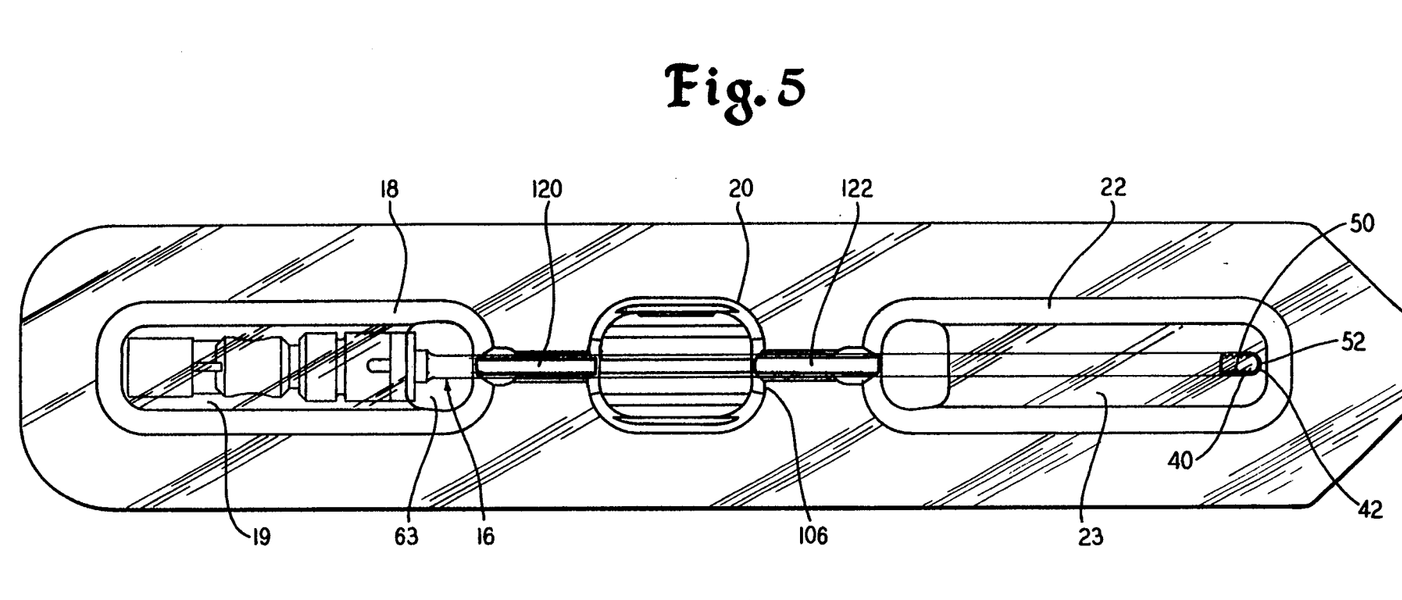
FIG. 5 is a plan view of FIG. 4.

FIGS. 1 through 3 show various views of a transparent blister package or container 10 formed in accordance with the principles of this invention. Package 10 is shown empty in FIGS. 1-3 for clarity, although it will be understood that the package would appear similar if it contained a device and was formed of an opaque material. FIGS. 4 and 5 show a transparent package 10 containing a product, for example, an elongated arthroscopic shaver blade 16. Package 10 is integrally formed to have a hollow housing 11 provided with an internal cavity 12 surrounded by a peripheral flange 14. Housing 11 is elongated in order to receive an elongated product such as arthroscopic shaver blade 16 and comprises first and second housing sections 18 and 22 at opposing ends of the package and a trigger section 20 situated around the longitudinal midpoint between opposing housing sections 18 and 22. Interposed between first housing section 18 and trigger 20 is a transition section 24 and a locking station 26, the purpose of which will be described below. Similarly, interposed between housing section 22 and trigger section 20 is a transition section 28 and a locking station 30. All housing sections 18 through 30 and the cavity sections formed thereby are longitudinally aligned along the axial plane 32 of package 10 and are contiguously joined in order to form one open cavity for receiving an elongated product. Axial plane 32 is the axial plane of symmetry intersecting the center line 32 in FIG. 3 and extending out of the plane of the drawing.

Package 10 may be formed from polyethylene, polyvinyl chloride or any other polymeric material suitable for sterile packaging. In the preferred embodiment, the cavity is thermo formed from a 0.020" PETG film. The thickness and type of material may obviously be changed to accommodate different products.

As best seen in FIG. 4, housing sections 18 and 22 define open spaces 19 and 23, respectively, within cavity 12 for receiving an end of an elongated device in a cantilevered manner. This is a particularly useful configuration for devices such as arthroscopic shaver blades or drills which have a sharp cutting edge at one end. Arthroscopic shaver blade 16 is shown as an example of the type of known elongated device that may be stored in package 10 and forms no part of this invention. Shaver blade 16 has an elongated outer member 34 and a rotatable elongated inner member 44. Outer member 34 has a proximal hub 36 and an elongated outer tube 38 provided with an opening 40 at its distal tip 42. Inner member 44 has a proximal hub 46 and an elongated inner shaft 48 provided with a cutting edge 50 at its distal tip 52. The invention enables each end of shaver blade 16 to be held within its own respective housing section 18 and 22 in a cantilevered manner such that the blade's proximal-most end (i.e. hubs 36 and 46) and distal-most end (i.e. ends 42 and 52) are spaced from adjacent interior surfaces of the peripheral walls of housing sections 18 and 22, respectively.

The proximal wall 54 of housing section 18, i.e. that portion of section 18 abutting transition section 24 and being closest to the longitudinal midpoint or transverse central plane 56 of package 10 is positioned to limit the longitudinal motion of shaver blade 16 due to interference between wall 54 and hub 36. (Note that FIG. 4 is not necessarily shown to scale.) The inner distal walls 56 and 58 at opposite ends of the package can also limit longitudinal motion for those products which could be allowed to touch interior cavity surfaces without deleterious effects.

Figure 7:
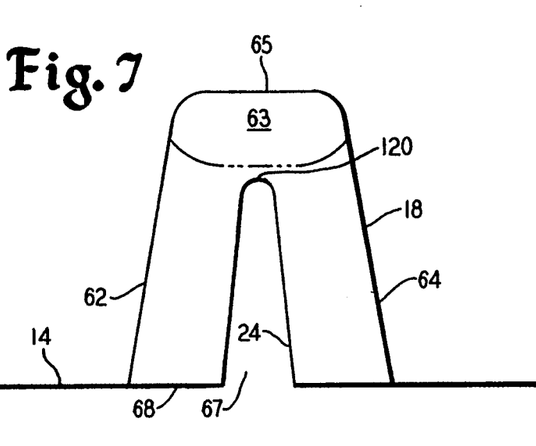
FIG. 7 is a cross-sectional view of FIG. 2 taken along the lines 7—7.

Cavity 12 has a peripheral wall 60 which generally extends transversely upwardly from flange 14 at a predetermined draft angle as best seen in FIGS. 1–3. The positive draft angle of cavity wall 60 facilitates not only its manufacture but, as will be understood below, the placement within cavity 12 of different diameters of cylindrical devices. To facilitate the description of the invention, the vertical dimension shown in FIG. 2, i.e. extending upwardly from, the plane of flange 14, will be referred to as the "transverse" direction while the vertical dimension in FIG. 3, i.e. extending perpendicularly to the longitudinal axial plane 32 of the package, and within planes parallel to the plane of flange 14, will be referred to as the "lateral" direction. As best seen in FIGS. 2, 3 and 7, cavity wall 60 has a generally trapezoidal cross-section with symmetrical, longitudinally extending opposing side walls 62 and 64 on opposite sides of axial plane 32, the side walls being pinched in toward each other in the vicinity of transition sections 24 and 28 and locking sections 26 and 30. The contour of wall 60 varies smoothly at the junctions between the various sections 18 to 30 of housing 11. A sloping wall 63 faces toward the longitudinal center of the package and, as will be understood below, helps in pushing products from package 10 such as the smallest diameter arthroscopic shaver blades received in product-retention sections 74 and 84 identified below. Wall 60 has a closed top end 65, end walls 66a and 66b, an open bottom end 67 surrounded by a peripheral bottom rim 68 between flange 14 and the transversely extending portions of the side walls 62, 64 and end walls 66a, 66b.

Figure 6:
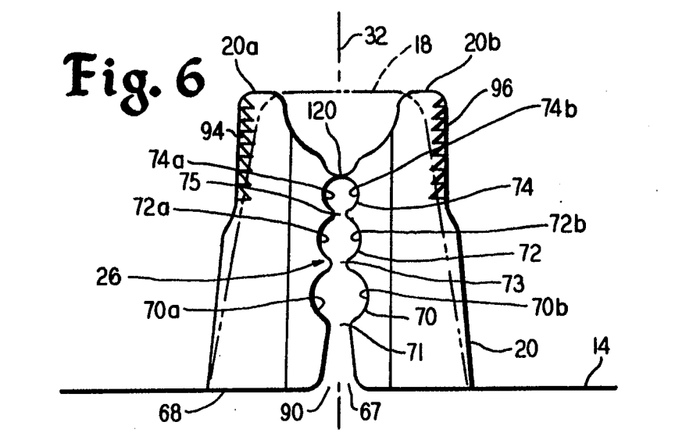
FIG. 6 is a cross-sectional view of FIG. 2 taken along the lines 6—6.

As best seen in FIGS. 1, 2 and 6, locking stations 26 and 30 comprise a plurality of circularly profiled product-retention sections 70, 72, 74 and 80, 82, 84, respectively. Each section comprises opposing, arcuate, device-contacting wall surfaces associated with the two symmetrical "a" and "b" housing halves or sides of housing 11 on opposite sides of the longitudinal plane of symmetry 32. Side wall 62 is the "a" side and carries components having an "a" in their identifying number, and side wall 64 is the "b" side. This product-retention section 70 comprises wall surfaces 70a and 70b, section 72 comprises wall surfaces 72a and 72b and section 74 comprises wall surfaces 74a and 74b. While device-contacting surfaces could be formed as a single pair of surfaces (e.g. 70a and 70b) in order to retain an elongated device at a single point intermediate along its length, in the preferred embodiment, two longitudinally spaced pairs of device-contacting surfaces are utilized to support the elongated device at two longitudinally spaced points along its length. Actually, the contact between each wall surface and the device is not a "point" contact, but has a defined axial length discussed below with respect to FIG. 12. Furthermore, the shape of the device-contacting surfaces is concave in order to more conformably engage a cylindrical portion of the elongated device. Locking station 30 is similar in structure and will not be described in detail except to say that its product-retention sections 80, 82 and 84 provide the other of the longitudinally spaced pairs of device-contacting surfaces. Thus, the operative spaced pairs are formed by aligned sections 70/80, 72/82 and 74/84.

Figure 9:
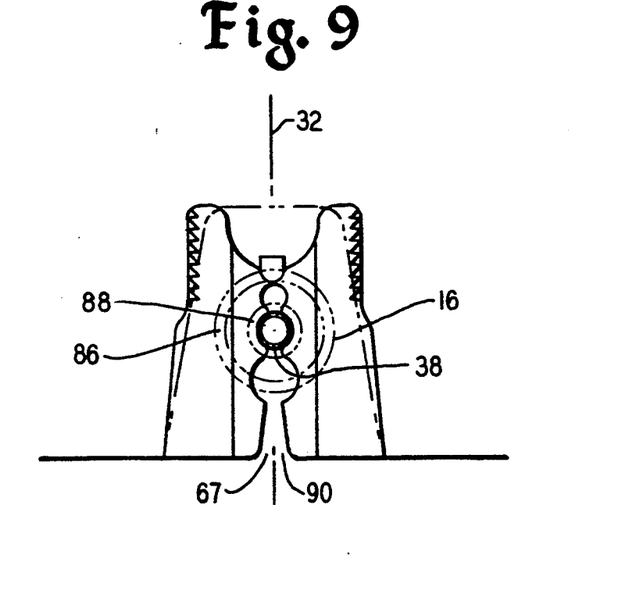
FIG. 9 is a cross-sectional view of FIG. 4 taken along the lines 9—9.

The sections of each locking station 26 and 30 are contiguous and of decreasing diameter extending transversely outwardly from the plane of flange 14. The bottom-most portion of each section (for example, 70, 72 and 74) is formed by a pair of longitudinally extending and opposing rounded edges or surfaces normally laterally spaced from each other by gaps 71, 73 and 75, respectively. Gaps 71, 73 and 75 are normally smaller than the diameter of the cylindrical product retained in the corresponding section until they are increased during the process of releasing a product as will be discussed below. Locking stations 26 and 30 are, in the preferred embodiment, longitudinally symmetrical about midpoint 56 and activation of trigger section 20 will operate on both locking stations simultaneously. Such symmetry is not necessarily required and the actual structure of a trigger section and an associated locking station or stations is dependent upon the product to be retained and the materials used to form the package. As best seen in FIGS. 4 and 9, an elongated cylindrical product such as shaver blade 16 may be placed into cavity 12 by being pushed past the openings 90 and 92 of locking stations 26 and 30, respectively, and into frictional engagement with either product-retention section pairs 70/80, 72/82 or 74/84 depending upon the diameter of the cylindrical object. The shaft of the elongated device to be held in package 10 must be relatively rigid to enable a friction fit within the selected group of arcuate wall sections.

In FIG. 9 concentric circular surfaces 86 and 88 represent structural components of the hub 36 of outer tubular member 34. In the preferred embodiment the diameters of the arcuate section pairs 70/80, 72/82 and 74/84 are chosen to enable package 10 to retain a disposable or limited re-use arthroscopic surgical shaver blade having a diameter of either 3.5 mm, 4.2 mm or 5.5 mm, respectively. Those skilled in the art will understand that the arcuate length (i.e. the arc length in transverse cross-section) of each section pair 70/80, 72/82 and 74/84 is a function of the size and weight of the object to be retained in the package. It should be understood that the arcuate length of the wall surfaces of locking station 26 need not equal that of the wall surfaces of locking station 30, depending upon the structure of the device to be retained.

Figure 8:
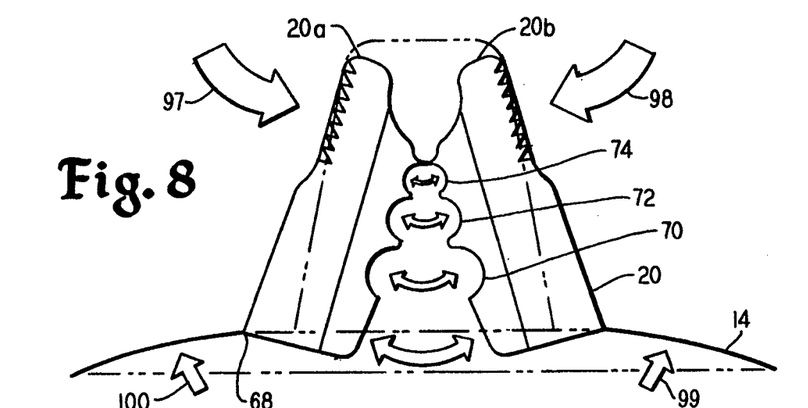
FIG. 8 is a view of FIG. 6 showing the position of portions of the package during the process of releasing an object from the package.

The product releasing mechanism will now be described. As best seen in FIGS. 1, 6 and 8, trigger section 20 comprises laterally spaced finger tabs 20a and 20b on opposite sides of axial plane 32. Finger tabs 20a and 20b are integrally formed at the end of trigger section 20 distal-most from the plane of flange 14 and have indented and grooved tactile areas 94 and 96. The size and arrangement of finger tabs 20a and 20b facilitates one-handed operation of the trigger means although a variety of modifications may be made to this structure to accommodate various goals. For example, for larger or heavier products, it may be desirable to longitudinally lengthen the tabs to accommodate two-handed operation or to extend them transversely for greater leverage.

Figure 10:
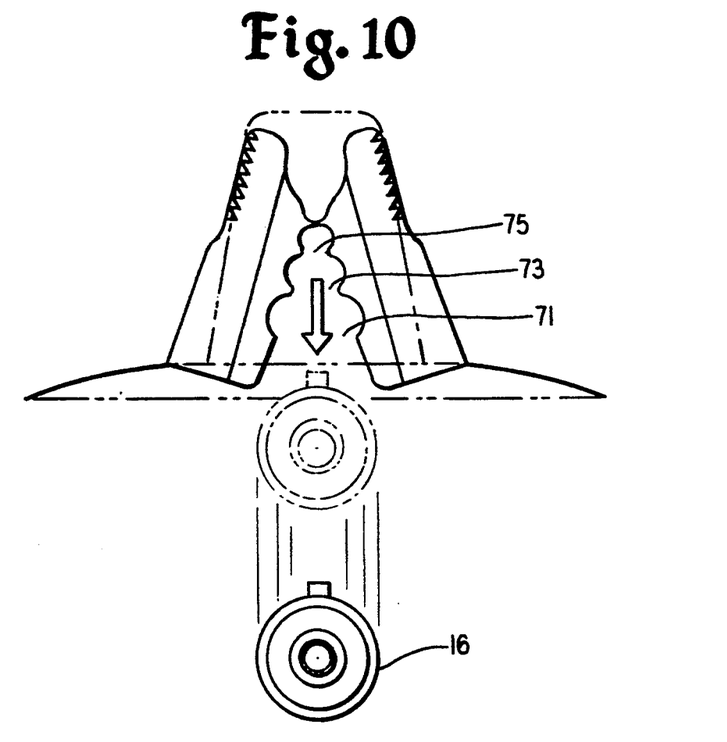
FIG. 10 is a view of FIG. 9 showing the position of portions of the package during the process of releasing an object from the package.
Figure 11:
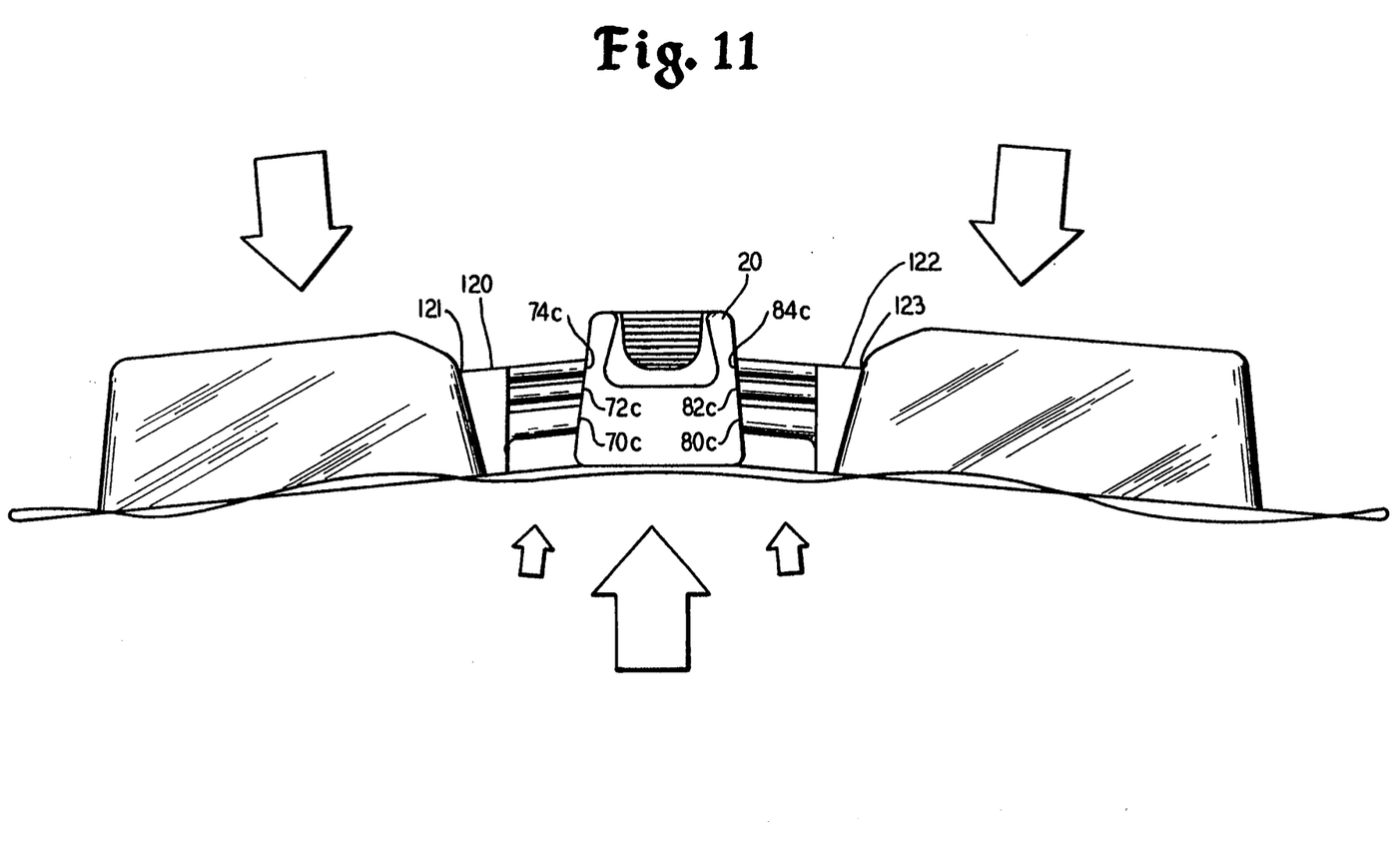
FIG. 11 is a diagrammatic side elevation of the package of FIG. 1 showing the possible deformation of the package during the process of releasing a product.
Figure 12:
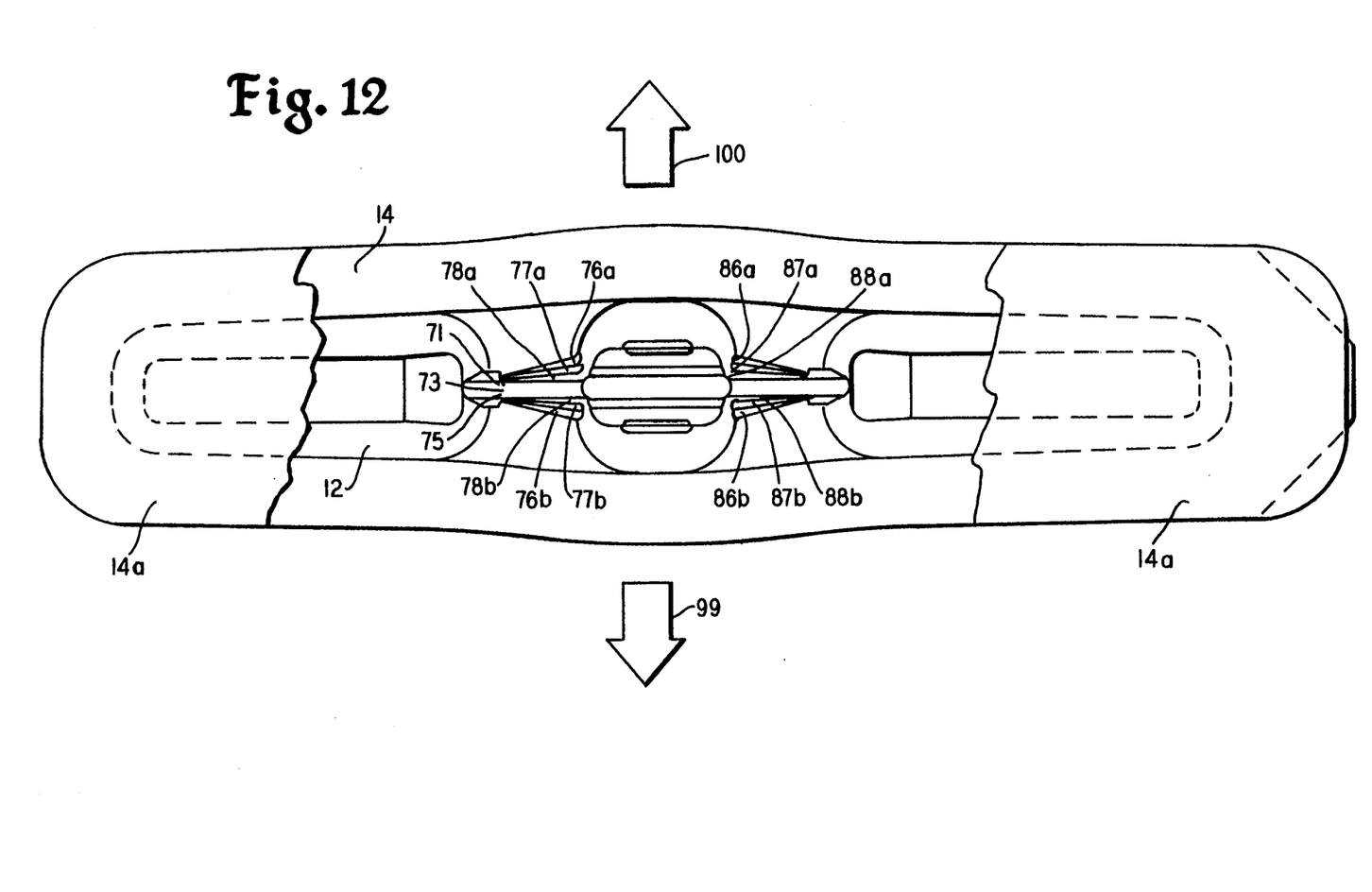
FIG. 12 is a diagrammatic bottom plan view of the package of FIG. 1 showing the possible deformation of the package during the process of releasing a product.

The operation of the product releasing action of the invention is explained by reference to FIGS. 8 through 12 showing the possible deformation of various portions of package 10 during the process of releasing a product from the package. The material of the body portion of trigger section 20 serves as an interconnecting means to join finger tabs 20a and 20b to the "a" and "b" sides of locking stations 26 and 30. As tabs 20a and 20b are squeezed toward each other in the direction of arrows 97 and 98 (FIG. 8), the distance between opposing components on the "a" and "b" sides increases and the proximal ends of trigger section 20 near flange 14 on each side "a" and "b" of the package move laterally away from each other, thereby pushing adjacent, central portions of flange 14 in the direction of arrows 99 and 100 (FIGS. 8 and 12). As best seen in FIG. 11, the end portions of flange 14 remain relatively unaffected at small degrees of motion of the central part of the flange. The movement of the central portions of flange 14 causes "a" and "b" sides of the longitudinally centermost ends of section pairs 70/80, 72/82 and 74/84 to move laterally away from each other as best seen in FIG. 12. The center-most ends of sections 70, 72 and 74 are identified as facing surfaces 76a/76b, 77a/77b and 78a/78b. Similarly, the center-most ends of sections 80, 82 and 84 are identified as facing surfaces 86a/86b, 87a/87b and 88a/88b. Further inward motion of tabs 20a and 20b will cause the distal ends of section pairs 70/80, 72/82 and 74/84 to move laterally away from each other until the minimum size of gaps 71, 73 or 75 is made large enough to enable a product retained within the grooves to fall out (FIG. 10).

It will be understood from FIG. 12 that flange 14 contributes to the security of product retention when a lid 14a is sealingly engaged with the flange. Lid 14a has substantially the same size as undeformed flange 14 and, therefore, prior to removal of lid 14a it prevents the opposing central sides of flange 14 and the adjacent parts of peripheral wall 60 (adjacent trigger 20) from moving away from each other thereby preventing accidental activation of trigger 20.

In the preferred embodiment, each of the sections 70, 72, 74 and 80, 82, 84 have the same axial length 102 although, as best seen in FIG. 4, the proximal ends of the sections, that is, the ends terminating at trigger boundary walls 104 and 106 closest to trigger section 20, are angled toward the longitudinal center of the package as shown by line 108 which is aligned with surface 104. The distal ends of sections 70, 72, 74 and 80, 82, 84 follow the boundary walls 110 and 112 between transition sections 24 and 28 and the adjacent locking station. If the length of each section of section pairs 70/80, 72/82 and 74/84 was too great, the trigger releasing action of finger tabs 20a and 20b would be compromised because the distal ends of the section pairs would require more laterally inward motion of the finger tabs before opening sufficiently to release a product. There is a relationship between the size and spacing of the finger tabs and the associated gaps which may be produced in any given package design.

FIG. 11 attempts to diagrammatically show a possible deformation of flange 14 and other parts of housing 11. As best seen in FIG. 11, a cylindrical elongated product retained in the smallest grooves 74/84, in addition to being released by the laterally outward movement of surfaces 74a and 74b, will also be urged transversely out of cavity 12 by the downward motion of the distal ends 121 and 123, top edges 120 and 122, respectively. Edges 120 and 122 join opposing lateral sides of locking stations 26 and 30 on each side of axial plane 32.

It will be noted that the invention provides direct engagement between the elongated device and the inner wall surfaces of section pairs 70/80, 72/82 or 74/84. Consequently, there is no necessity for auxiliary inserts or the like and, therefore, no possibility of such inserts falling into the surgical field when the package is opened.

While the invention has been described in terms of a package for containing an elongated medical instrument, it is equally suitable for other elongated medical products and elongated products in general.

The structure of the preferred embodiment lends itself to the storage of devices which have a main elongated tubular body of a given size and other associated component parts of other sizes and/or shapes. In addition to the aforementioned arthroscopic shaver blades, devices such as endoscopes or arthroscopes may be suitable. The principles of this invention could be adapted to a variety of elongated packages having housing or cavity sections designed to accommodate the particular dimensions of the product.

It will be understood by those skilled in the art that numerous improvements and modifications may be made to the preferred embodiment of the invention disclosed herein without departing from the spirit and scope thereof.

What is claimed is:

1. A storage container for containing an elongated product comprising:
   a housing having an elongated cavity for receiving an elongated device along an axial plane thereof, said cavity defined by a peripheral wall having a closed top end, a bottom rim surrounding an open bottom end and a side wall extending between said top end and said bottom rim;
   locking means for releasably, frictionally and directly engaging an elongated device within said housing, said locking means integrally formed with said peripheral wall of said housing; and
   a trigger means for being selectively actuated to release said locking means to thereby disengage an elongated device engaged by said locking means, said trigger means comprising:
      a pair of laterally spaced finger tabs integrally molded with said closed top end of said peripheral wall, one on each side of said axial plane; and
      interconnecting means for joining said pair of finger tabs and said locking means to enable motion of said pair of tabs to disengage the locking means.

2. A container according to claim 1 further comprising:
   a peripheral flange surrounding said bottom rim; and
   a lid sealingly secured to said flange.

3. A container according to claim 1 wherein said locking means comprises at least one pair of opposed wall sections of predetermined axial length extending laterally inwardly from opposite sides of said peripheral wall and normally spaced a predetermined lateral distance for thereby frictionally engaging a portion of an elongated device between said opposed wall sections.

4. A container according to claim 3 wherein said opposed wall sections engage an elongated device at at least one intermediate point along its length.

5. A container according to claim 3 wherein said locking means comprises an inwardly facing device-contacting surface on each of said opposed wall sections for conformably engaging a portion of an elongated device.

6. A container according to claim 5 wherein said inwardly facing device-contacting surface has a concave arcuate profile in order to engage an elongated device having a circular cross-section.

7. A container according to claim 1 wherein said housing is integrally formed and wherein said interconnecting means comprises a predetermined portion of said housing between said trigger means and said locking means.

8. A container according to claim 1 wherein said housing comprises longitudinally symmetrical housing halves integrally formed together and symmetrical about said axial plane and wherein said locking means comprises at least one longitudinally spaced and aligned pair of locking stations, each locking station comprising a pair of arcuate wall sections comprising a first member and a second member longitudinally extending and laterally opposed from each other on opposite sides of said axial plane, spaced a predetermined lateral distance and movable laterally away from each other to increase said predetermined lateral distance upon activation of said trigger means.

9. A container according to claim 8 wherein each of said locking stations comprises:
   a first opposed pair of concave-profile walls defining a cylindrical space therebetween having a first predetermined diameter and a bottom predetermined lateral gap between the longitudinally extending, laterally inward-most opposed surfaces of said first pair of opposed concave-profile walls;
   a second opposed pair of concave-profile walls defining a cylindrical space therebetween having a second predetermined diameter and a bottom predetermined lateral gap between the longitudinally extending, laterally inward-most opposed surfaces of said second pair of opposed concave-profile walls;
   a third opposed pair of concave-profile walls defining a cylindrical space therebetween having a third predetermined diameter and a bottom predetermined lateral gap between the longitudinally extending, laterally inward-most opposed surfaces of said third pair of opposed concave-profile walls;
   said first predetermined diameter being greater than said second predetermined diameter and said second predetermined diameter being greater than said third predetermined diameter.

10. A container according to claim 9 wherein said first opposed pair of concave-profile walls is closer to said bottom rim than said third opposed pair of concave-profile walls.

11. A container according to claim 8 wherein said trigger means is resilient and said pair of finger tabs are formed as
   a first tab integral with one of said longitudinally symmetrical housing halves; and
   a second tab integral with the other of said longitudinally symmetrical housing halves.

12. A container according to claim 1 wherein said housing comprises:
   first, second and third longitudinally aligned cavity sections each having a first predetermined lateral opening size at said bottom rim;
   wherein said locking means comprises:
   a first locking station interposed between said first and second cavity sections, said first locking station having a first predetermined lateral opening size at said bottom rim;
   a second locking station interposed between said second and third cavity sections, said second locking stations having a second predetermined lateral opening size at said bottom rim, said first and second locking stations each having at least one pair of opposed, longitudinally extending wall sections, transversely spaced from said bottom rim, for engaging an elongated product; and
   wherein said trigger means comprises:
   a pair of laterally spaced and transversely and longitudinally extending finger tabs;
   whereby, when said finger tabs are moved laterally toward each other, predetermined portions of said peripheral wall of said second cavity section move laterally away from each other to thereby move opposing wall sections of said locking stations away from each other.

13. A container according to claim 12 further comprising said housing being longitudinally symmetrical about a transverse plane through the longitudinal midpoint of said second cavity section.

14. A container according to claim 12 wherein said housing has a generally trapezoidal cross-section in at least one of said first, second or third cavity sections.

15. A storage container for containing an elongated product having a first end and a second end comprising:
   a housing having an elongated cavity provided with an enlarged space along the length of said cavity;
   means for enclosing said cavity to seal said enlarged space from the ambient;
   locking means integrally formed with said housing for releasably, frictionally and directly engaging a predetermined portion of said elongated product in order to maintain at least one of said first end or said second end cantilevered within said enlarged space;
   a trigger means for being selectively actuated to release said locking means to thereby disengage an elongated device engaged by said locking means, said trigger means comprising:
   a pair of laterally spaced finger tabs integrally molded with said housing; and interconnecting means for joining said pair of finger tabs and said locking means to enable motion of said pair of tabs to disengage the locking means.

16. A method of storing an elongated medical device in a container and selectively releasing the device from the container comprising the steps of:
   (a) providing an elongated housing for receiving an elongated medical device, said housing having an axial plane;
   (b) providing in said housing at least one pair of opposing, integrally formed, inwardly extending wall sections said wall stations normally spaced a predetermined distance for engaging the device on each lateral side of said axial plane;
   (c) providing on said housing, on each lateral side of said axial plane an integrally formed trigger tab means operatively connected to said wall sections;
   (d) inserting an elongated device into said housing in direct engagement with said wall sections;
   (e) moving each of said trigger tab means toward the axial plane to increase said predetermined distance and thereby disengage a device engaged by said wall sections.

* * * * *